United States Patent [19]

De

[11] Patent Number: 5,004,724
[45] Date of Patent: Apr. 2, 1991

[54] SUPERCONDUCTIVE QUANTUM INTERFERENCE DEVICE FOR THE NON-DESTRUCTIVE EVALUATION OF METALS

[75] Inventor: Dilip K. De, Winston-Salem, N.C.

[73] Assignee: International Superconductor Corp., Riverdale, N.Y.

[21] Appl. No.: 321,263

[22] Filed: Mar. 9, 1989

[51] Int. Cl.$^5$ .............................. G01N 27/82
[52] U.S. Cl. ........................ 505/1; 324/240; 324/248; 505/702
[58] Field of Search ............... 324/248, 239–243, 324/234, 236, 238, 237; 505/702, 849, 843, 845, 846, 701, 705; 428/930

[56] References Cited

U.S. PATENT DOCUMENTS

| | | | |
|---|---|---|---|
| 3,976,934 | 8/1976 | Voigt et al. | 324/224 |
| 4,243,939 | 1/1981 | Grossman et al. | 324/242 X |
| 4,352,065 | 9/1982 | Rogachev et al. | 324/240 X |
| 4,437,064 | 3/1984 | Overton, Jr. et al. | 324/248 X |
| 4,481,471 | 11/1984 | Miller et al. | 324/240 |
| 4,628,261 | 12/1986 | Huschelrath et al. | 324/240 |
| 4,639,675 | 1/1987 | Hinton | 324/248 X |
| 4,677,379 | 6/1987 | Arnaud et al. | 324/240 X |
| 4,706,021 | 11/1987 | Chamuel | 324/240 X |
| 4,788,504 | 11/1988 | Blanpain et al. | 324/243 X |
| 4,851,776 | 7/1989 | Goto et al. | 324/248 |

Primary Examiner—Reinhard J. Eisenzopf
Assistant Examiner—Warren S. Edmonds
Attorney, Agent, or Firm—Herbert Dubno

[57] ABSTRACT

High-$T_c$ superconductor quantum interference devices (SQUIDs) for noise-free, accurate measurements of defects and flaws in metal shapes and forms by measuring changes in the secondary magnetic field intensity around any point which is excited by a primary excitation current or by measuring changes in the impedance of the exciting coils. These measured changes are correlated to defects and flaws present in the metal.

15 Claims, 5 Drawing Sheets

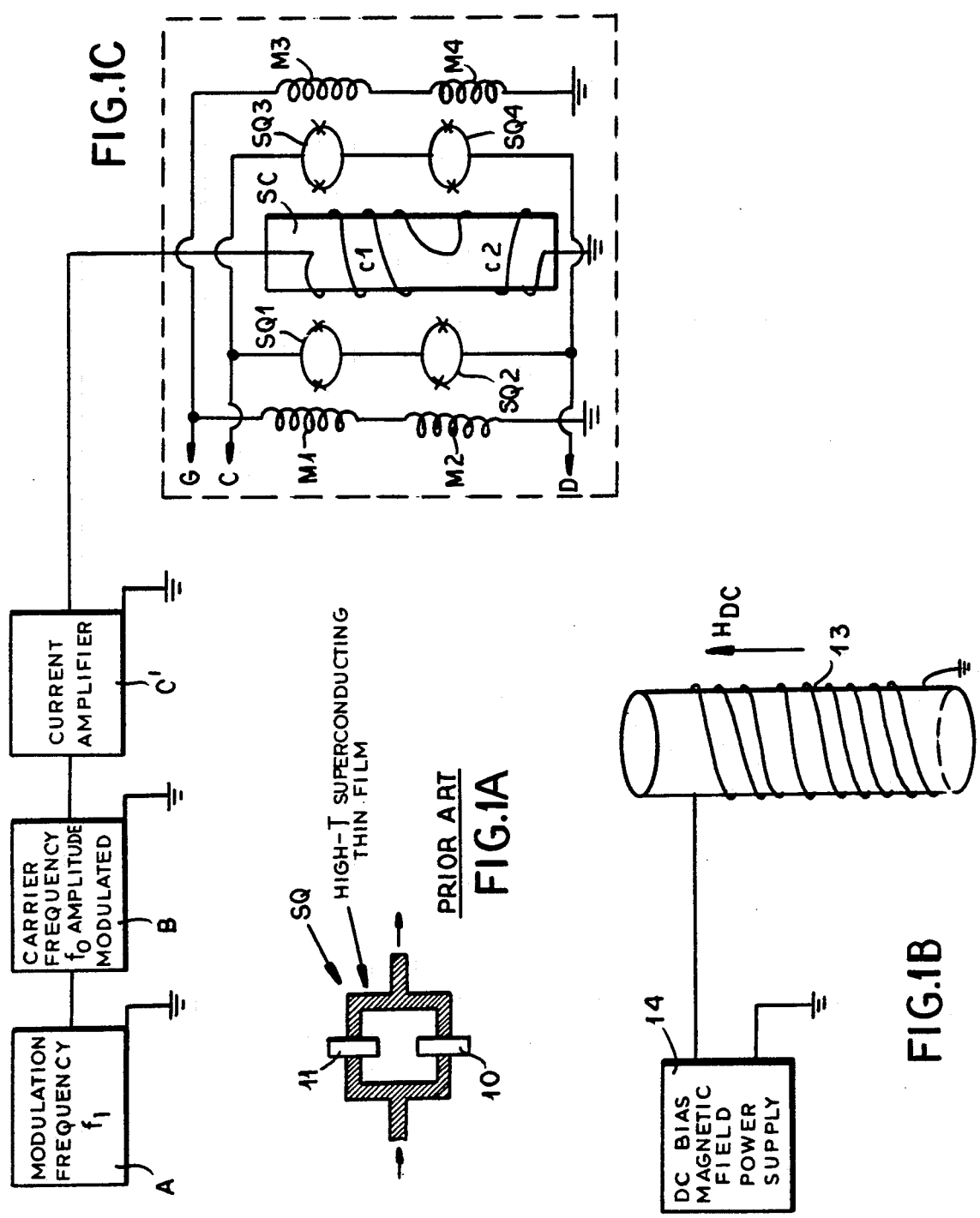

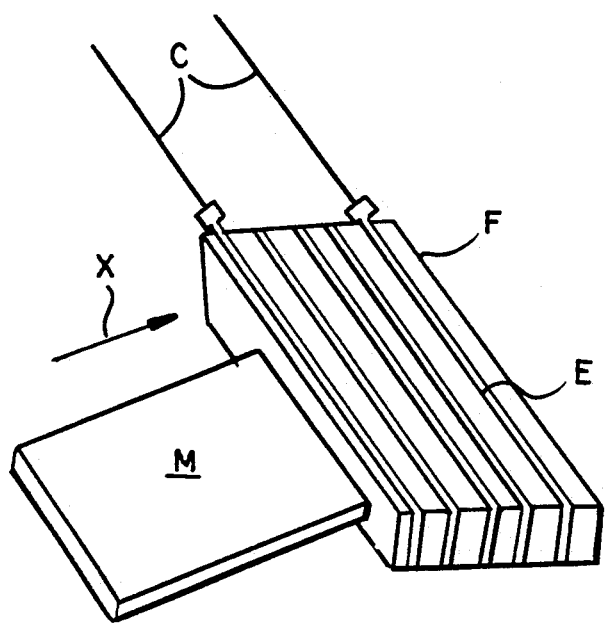
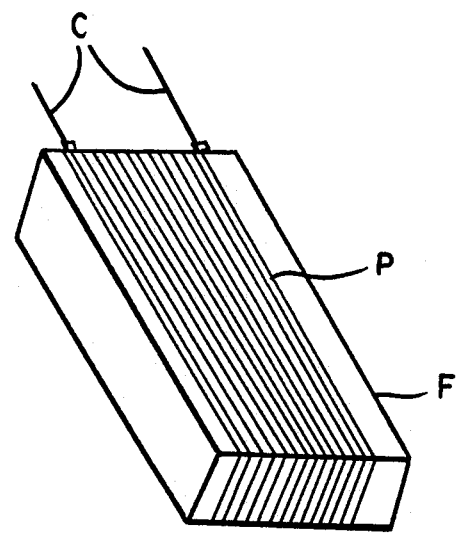
FIG.5A          FIG.5B
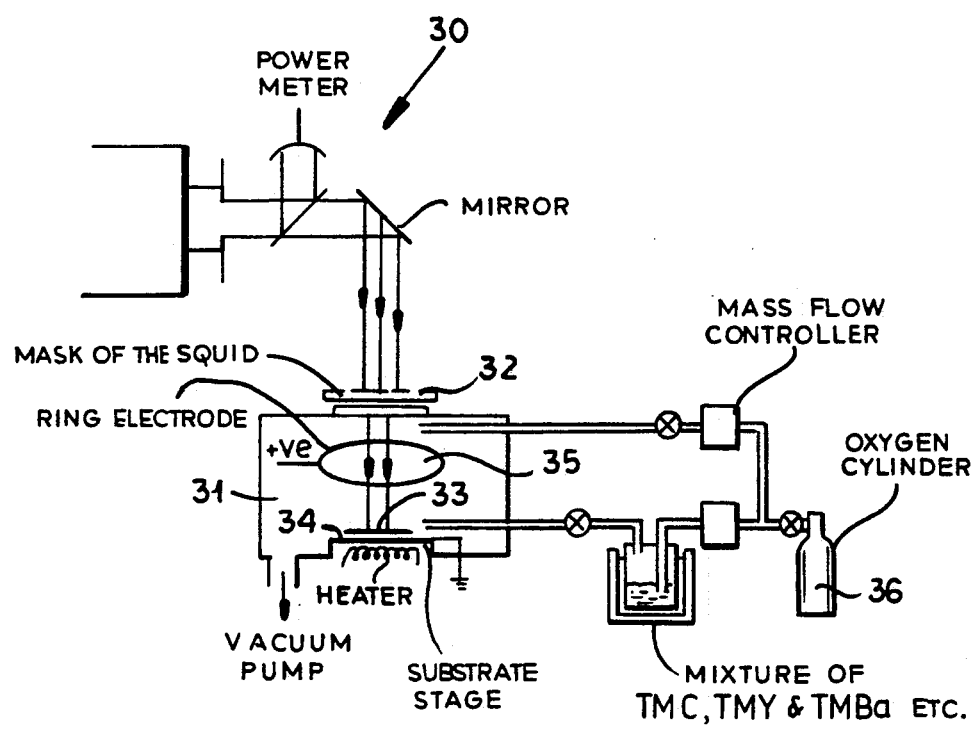
FIG.8

SUPERCONDUCTIVE QUANTUM INTERFERENCE DEVICE FOR THE NON-DESTRUCTIVE EVALUATION OF METALS

FIELD OF INVENTION

This invention relates to non-destructive evaluation of metals, based on the detection of (a) change in impedance of exciting coils placed near the surface of a metallic specimen or a change in secondary flux resulting from the defects and flaws of a metal. More particularly the invention relates to high temperature superconducting interference devices for this purpose.

BACKGROUND OF THE INVENTION

Superconductivity was originally discovered by the Dutch scientist Heike Onnes in 1911 while he was studying the electrical properties of mercury at very low temperatures. In more recent times, Ogg (1946) studied superconductivity in ammonia solutions and proposed that superconductivity arose in these quenched metal-ammonia solutions because of mobile electron pairs. About 1973, it was determined that certain niobium metal alloys exhibited superconductivity when cooled to liquid helium (4° K.) temperatures. Later results in the 1970's raised this temperature as high as 23° K. (−250° C.). Until recently, it was believed that superconductivity above this temperature was not possible. This belief was based on the theoretical work of Bardeen, Cooper and Schieffer (BCS theory-1946) which predicted such a limit. In December 1986, Bednorz and Muller announced the discovery (G. Bednorz and A. Mller, Z. Phys., B64 189 (1986)) of a new ceramic superconducting compound based on lanthanum, barium, and copper oxides, whose critical temperature for superconductivity was close to 35° K. By the following month, the critical temperature, Tc, for the onset of superconductivity was raised to nearly 80° K. by C. W. Chu and coworkers (M. K. Wu, J. R. Ashburn, C. J. Tang, P. H. Hor, R. L. Meng, L. Gao, Z. J. Huang, Y. Q. Wang and C. W. Chu, Phys. Rev. Lett. 58 908 (1987)). This was achieved by changing the composition to yttrium barium copper oxide, approximated by the formula: $Y_{1.0}Ba_{1.8}Cu_{3.0}O_{6.3}$. Since then, a number of families of superconducting ceramic oxides have been investigated, including:

Bismuth Strontium Calcium Copper Oxide:
$Bi_2Sr_{3-x}Ca_xCu_2O\ 8+y2$
$T_c = 114°$ K.

Thallium Calcium (Barium) Copper Oxide:
Tl $Ba_2Ca\ Cu_2O_7$
Tl $Ba_2Ca_2Cu_3O_9$
Tl $Ba_2Ca_3Cu_4O_{11}$
Tl $Ba_2Ca_4Cu_5O_{13}$
Tc = 120° K.
$BaO-K_2O-Bi_2O_3$
Tc = 30 K.

There have been some scattered reports of superconductivity above 162 K., For instance, R. G. Kulkarui has reported superconducting oxides having an approximate composition 0.5 CaO. 0.5 ZnO. $Fe_2O_4$, with critical temperatures in this range. Ogushi also reported superconductivity at room temperature in yet ill-defined niobium strontium lanthanum oxides. While these reports have yet to be confirmed independently by other researchers, it is reasonable to expect that superconductors with critical temperatures near to room temperature will soon be obtained.

Niobium-based superconducting alloy wires have long been used for detecting small changes in magnetic field strength. In the prior art, the non-destructive evaluation of defects in metals employs an eddy current technique wherein the impedance change of the primary exciting coil is measured and correlated to the presence of defects and flaws within the metal sample. The method is cumbersome and must be carried out at liquid helium temperatures (∼4 K.), which is expensive. In this method of nondestructive evaluation, currents are caused to flow in a test specimen by placing it within, or in close proximity to, the primary magnetic field of a probe coil (or array of coils). In turn, these induced currents generate a secondary magnetic field, which, by Lenz's law, opposes the primary magnetic field, thus affecting the impedance of the probe or exciting coil. By using Green's function technique and the Born Approximation, one can demonstrate that the impedance of a single turn coil, which surrounds a conducting non-magnetic cylinder containing a flaw and/or defect, will depend on the size of said flaw, its conductivity, and its depth.

The change of impedance, DZ, due to the flaw is proportional to the change of conductivity $D\sigma = \sigma - \sigma_o$ and the square of the flaw length. The flaw depth affects the impedance change differently, depending upon the ratio of flaw position r', to the skin depth. In certain situations, some aspects of the geometry of the flaw can be determined by measuring the probe coil impedance as the probe coil is scanned across the surface containing the flaw.

I have determined that the use of superconductor quantum interference devices to measure flaws and defects in metals produces results much superior to any known heretofore, especially when said devices are used in conjunction with modulated high frequency exciting currents. This is accomplished through exciting coils placed around the metal plate, or wrapped around a cylinder. The arrangement of the SQUIDs includes an alternating bias current, and flux modulation in a locked flux-loop design. This mode of operation ensures minimum noise of voltages produced by the superconductor quantum interference devices, which may result because of critical current fluctuations in the non-identical junctions of the superconducting interference devices, and also because of fluctuations in junction resistances. I have further established that my new and novel methods for non-destructive detection of flaws in metals can be applied to both non-magnetic and ferric-magnetic materials, in contrast to the prior art. I have further determined that the technique of the instant invention is very sensitive, compared to those of the prior art.

OBJECTS OF THE INVENTION

Therefore, an object of this invention is to provide high-Tc superconductor quantum interference devices capable of measuring defects and flaws in any metal.

Another object is to provide a method of employing quantum interference devices to measure defects and flaws in any metal at sensitivities not heretofore possible. Still another object is to provide a method of evaluating flaws and defects in any metal which is much easier to apply and which produces results not possible before.

A final object is to provide improved of apparatus capable of employing superconductor quantum interference devices to measure and evaluate flaws and defects present in metals.

SUMMARY OF INVENTION

These objects are attained in a method of nondestructive evaluation of flaws in a metal body, comprising the steps of:
  (a) positioning a high-critical-temperature superconductive quantum interference device having a pair of insulated junctions in a superconductor loop in flux-sensing relationship to a location adjoining said body;
  (b) relatively displacing said body and said location;
  (c) while said body and said location are relatively displaced, exciting said body with a modulated alternating current and detecting with said device flux irregularities representing flaws in said body; and
  (d) establishing locations of said flaws by the relative positions of said location and said body upon the detection of said flux irregularities.

BRIEF DESCRIPTION OF THE DRAWINGS

The above and other objects, features and advantages of my invention will become more readily apparent from the following description, reference being made to the accompanying highly diagrammatic drawing in which:

FIG. 1A is a schematic illustration of a high-$T_c$ superconducting DC SQUID according to the invention;

FIG. 1B is a diagram which shows the bias magnetic field $H_{DC}$ is required for a ferromagnetic sample wherein the solenoid covers entirely the ferromagnetic sample;

FIG. 1C is a circuit diagram which shows the arrangement of the exciting coils c1 and c2, modulation coils M1, M2, M3 and M4 and the high-$T_c$ SQUIDs to measure the secondary fluxes that reveal the signature of defects and flaws in the metals;

FIG. 5a is a perspective view which shows schematically the primary exciting coil and insertion of a metal plate for evaluation of defects;

FIG. 5b is a perspective view which shows schematically the windings of the secondary coil P on the metal frame F that also contains the structure of FIG. 5a;

FIG. 8 is a diagram which shows schematically the arrangement to direct laser write high-$T_c$ superconducting interference devices on suitable substrates using the mask.

SPECIFIC DESCRIPTION

Figure 1E:
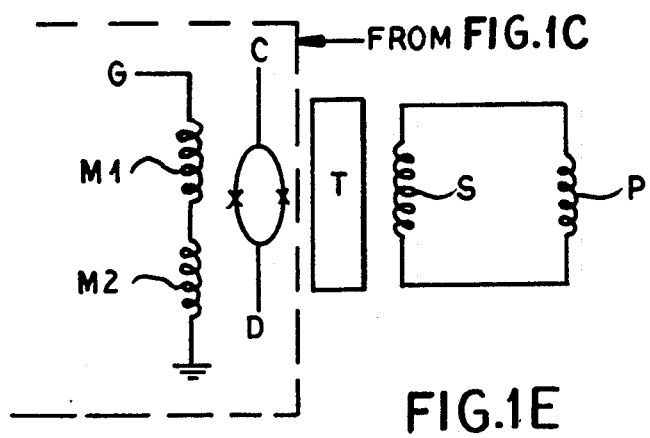
FIG. 1E is a circuit diagram which schematically how the SQUIDs can be placed remotely from the metals to be evaluated.
Figure 1F:
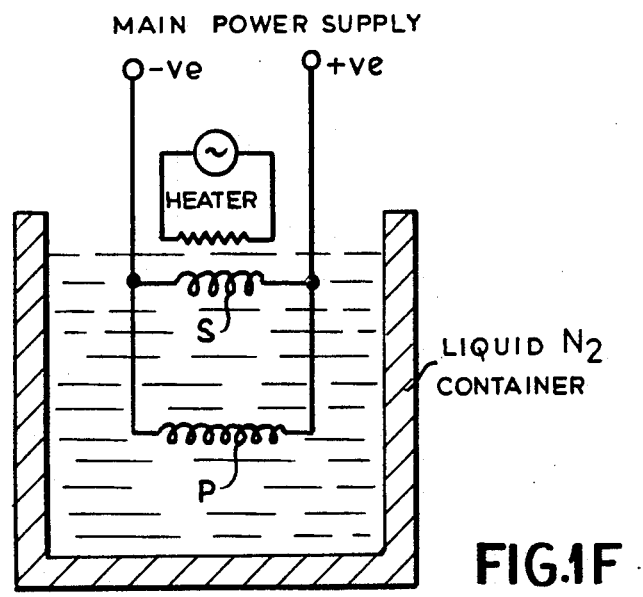
FIG. 1F is a sectional view which shows schematically the high-$T_c$ superconducting switch.
Figure 1D:
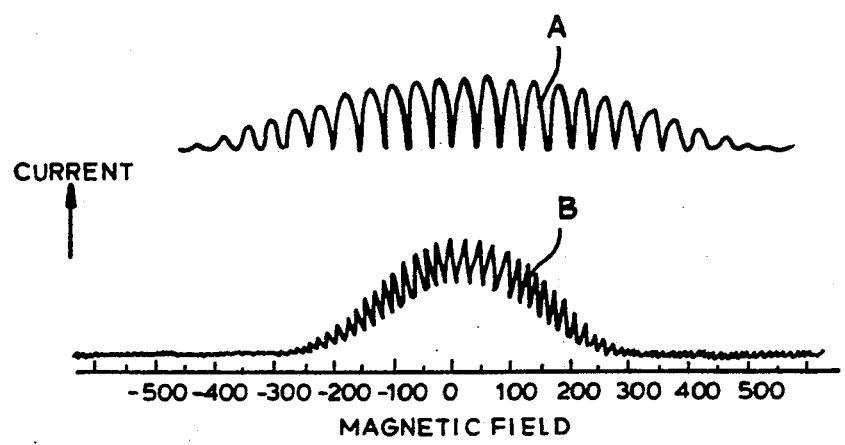
FIG. 1D is a graph which shows the interference and diffraction patterns observed in the current vs magnetic field applied to a dc SQUID as taken from a published paper.

This invention employs high critical temperature superconducting materials used in a device known as superconducting quantum interference device to detect flaws and defects in metals. Such a device (SQUID)s consists of two connected junctions 10, 11. The junctions are made of superconductor-insulator-superconductor. A typical schematic structure of such a device is shown in FIG. 1A. According o the macroscopic long range quantum interference effect of such a device, a total junction current can flow even in absence of any electric field or magnetic field. However, in presence of magnetic field $B_o$ applied perpendicular to the plane of the device (in FIG. 1A), the total maximum supercurrent shows interference effect as a function of $B_o$ as shown in FIG. 1D (Introduction to Solid State Physics, John Wiley & Sons, Inc, 1976, p. 394). It is because of this phenomena such a device is known as "superconducting quantum interference device". As can be seen from FIG. 1D, such devices can be easily employed to detect magnetic fields of a few milligauss. The smaller the junction area the more theoretically sensitive the device should be to detect smaller magnetic fields. This invention also relates to techniques of non-destructive evaluation of metals wherein said techniques are based on the effect of change in impedance of exciting coils, or change in the magnetic flux linking the said coil, placed near the surface of a specimen. Conventional SQUIDs thus far have not been successfully used for NDE because of the requirement of expensive liquid helium which also requires a special container.

Superconductor quantum interferometric devices are highly sensitive devices for detection of small changes of magnetic field or flux around any point and can be used very efficiently to detect flaws in metals, whether the said metals are magnetic or non-magnetic. When the exciting coils are modulated by an alternating current, eddy currents develop in the specimen and give rise to a secondary magnetic field. Defects and flaws present in the materials being measured act as perturbations to the said secondary magnetic fluxes, and result in changes in the resistance and reactance of the exciting coils. It is the measurements of either the change in impedance of the exciting coils or the secondary magnetic fluxes which allow for the establishment of specimen quality. Generally the change in the resistance is positive and the change in inductance is negative. For a non-magnetic specimen, the variation of the inclination angle of the exciting or probe coil (with respect to the surface of the conductor) has no influence on the reflected resistance. But the change in the reactance, as a function of inclination angle, is strongest for non-magnetic materials. For materials of poor electrical conductivity (which may be magnetic), high frequencies (of order of several KHz) are used; for materials of high electrical conductivity, low frequency excitations are used.

I have found that superconducting quantum interference devices are extremely sensitive, when used for the detection of small magnetic fluxes and magnetic fields. I have further established that the use of said devices markedly increases the limits of sensitivity of detection of changes in secondary magnetic field fluxes (and consequent detection of flaws and defects in metals) by several orders of magnitude over that previously known in the prior art. For example, the superconducting interference devices can detect fluxes which are integral multiples of the basic flux quantum, which is $2.0678 \times 10^{-7}$ gauss-cm$^2$. So far conventional SQUIDs have been made from $Nb_3Sn$ or NbTi superconductors with amorphous silicon dioxide or their oxides as insulators. Use of such SQUIDs require liquid helium which is expensive and require special container to operate. Moreover, when used for detection of magnetic fluxes, they exhibit a predominant 1/f noise which arise (i) either from an apparent flux noise or (ii) from the fluctuations of the conductance or critical current caused by charge trapping in the tunnel barrier (i.e., the superconductor-insulator junction). With the discovery of high temperature ceramic superconductors and the possibility of room temperature superconductors, high temperature superconductor quantum interference devices operating at 100 K. (and possibly at 300 K.) have become feasible. High-$T_c$ SQUIDs will be more advantageous to use than conventional helium SQUIDs, because of the high-critical temperature superconductor, the effect of thermal fluctuation on the critical current on the 1/f noise would be much smaller. Moreover following a first technique, the 1/f noise in the SQUID output current-voltages are almost completely eliminated. The first technique is termed as "Flux-loop-lock-modulation" with alternated bias currents. As part of the instant invention, I describe detailed techniques for the nondestructive evaluation of defects, flaws, and mechanical stress in non-magnetic metals in the form of a cylinder by using high-Tc superconductor quantum interference devices in the form of a ring. In some cases, modifications are required for cooling to 78 $K$. and cooling arrangements are not shown for the first technique.

FIG. 1B shows how a dc magnetic field can be produced by a solenoid 13 using a DC power supply 14.

As can be seen from FIG. 1C an oscillator A of frequency modulation $f_1$, feeds an oscillator B of carrier frequency $f_o$ amplitude modulated, and a current amplifier C'. The sample is the form of a cylinder (SC) in which flaws and defects are to be detected. Two sections of the primary exciting coils, c1 and c2 in series, are wrapped around the said cylinder, with said coils being wound in opposite directions. Coils c1 and c2 are fed by current from oscillator B of several KHz frequency. These currents are amplitude modulated by frequency $f_1$ (a few hundred Hz) fed from oscillator A. The said opposite windings cancel any undesirable high frequency pickup by the two pairs of high-Tc superconductor quantum interference devices: (sq1 and sq2) and (sq3 and sq4). These two pairs are connected in parallel, and their output goes to points C and D which are joined with those in FIG. 2. To simplify the procedure a single high-$T_c$ SQUID may alternatively be used. However use of a number of SQUIDs as shown in FIG. 1c enhances the sensitivity. For maximum sensitivity the SQUID plane should be normal to the axis of the coils. In this method, the operation of FIG. 1C is independent of the angular orientation of the test object about its axis which coincides with the axis of the coils c1 and c2.

Figure 2:
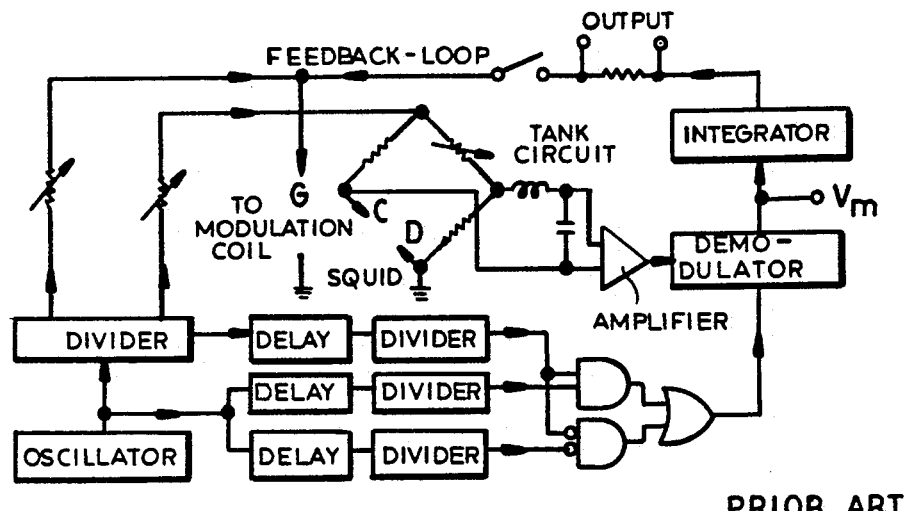
FIG. 2 is a block diagram which shows schematically the electronic circuits employed for noise free and accurate measurements of the fluxes by high-$T_c$ SQUIDs.

FIG. 2 shows the operational scheme of a dc superconductor quantum interference device (SQUID), coupled with flux modulation and biased alternating current which minimizes the voltage noise associated with critical current fluctuations of the junctions of the high-Tc superconductor quantum interference devices. This particular mode of use of SQUID has been published (S. Kuriki, M. Matsuda and A. Matachi J. Applied Phys. 64, 239 (1988)). Though the advantage of high-$T_c$ SQUID is that the noise due to thermal fluctuation of critical current would be smaller than the conventional SQUIDs (as discussed earlier), yet, because the superconductors are ceramic in nature, it would be difficult to make the superconductor-insulator-superconductor junctions all identical. Accordingly, critical current fluctuations will occur as a function of temperature. To overcome this and the problem due to thermal fluctuation of resistance of the SQUID junctions, a scheme of flux modulation and alteration of the bias currents (controlled by SQUARE WAVES of $f_m = \sim 150$ KHz and $f_b = f_m/8$) is applied. In this design of the instant invention, the superconductor quantum interference devices form one of the arms of a resistance bridge (FIG. 2). This reduces transient voltages associated with switching between $V^+(\phi)$ and $V^-(\phi)$. $\phi$ represents the magnetic flux that links the high-$T_c$ SQUIDs devices. This flux arises primarily from the excitation currents or the test cylinder containing the defects. The primary excitation currents generates secondary fluxes which depends on flaws and defects. The $V^+$ and $V^-$ are the voltages of a dc superconductor quantum interference device driven by positive and negative bias currents. It is this technique is termed "flux-locked-loop-modulation with alternating current bias". The said technique includes: modulation of a flux $\phi_o/4$ at the SQUIDs combined with alternating currents at a rate of $f_b << f_m$; The quantity $\phi_o$ is such that the following relations hold good for each junction of the SQUIDs. $2\pi I_c R^2 C/\phi_o = 0.5$ and $2LI_c/\phi_o = 1.0$ —where $I_c$, R and C are the critical current, shunt resistance and capacitance of a single junction of the high-$T_c$ SQUID and L is the inductance of the SQUID loop.

Figure 3:
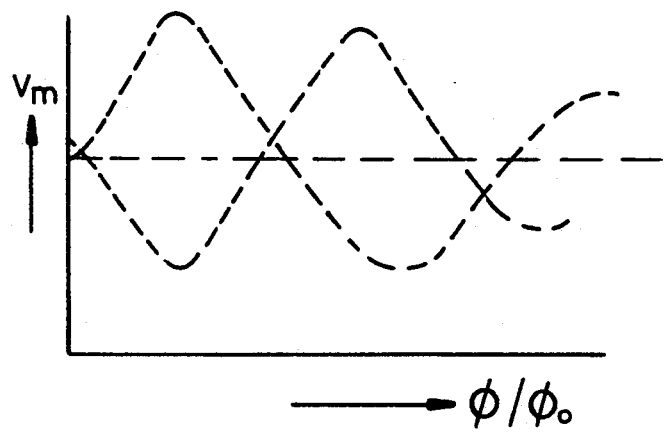
FIG. 3 is a graph which shows schematically the general variation of the modulated voltage $V_m$ with the magnetic flux ($\phi$) relative to the modulating flux $\phi_o$.

This would give rise to modulated SQUID output voltages $V_m{}^+(\phi)$ and $V_m{}^-(\phi)$. depending on the +ve and −ve bias currents. Subtraction between the modulated voltages of Vm$^+$ and Vm$^-$; and feed back of the (Vm$^+$ − Vm$^-$) as the flux after integration. The modulated voltage $V_m(L) = V(\phi + \phi_o/4) - V(\phi - \phi_o/4)$ occurs by a SQUARE. WAVE flux modulation of the output voltage of the SQUID. The + and − signs refer to the positive and negative bias currents. The advantage of this scheme is that it automatically gets rid of the shift of asymmetrical fluctuation of the junction so that the subtraction of $V_m{}^-$ from $V_m{}^+$ can be performed at the demodulator by using a reference signal that has a negative phase during the period of the negative bias current. The general variation of $V_m(\phi)$ with $\phi$ is shown in FIG. 3. Block B in FIG. 1B is necessary only when the specimen is a ferromagnetic sample. This is to generate a bias dc magnetic field parallel to the axis of the cylinder. The corresponding coils may be wrapped around the cylinder. These bias coils may also be made of flexible high-$T_c$ superconducting wires or tubes as invented by the author (See Ser. No. 07/300,287 filed 19 Jan. 1989). In such cases the bias magnetic field could be permanent in nature. Techniques are already known in the art to set up magnetic field in persistent mode of operation.

Figure 7:
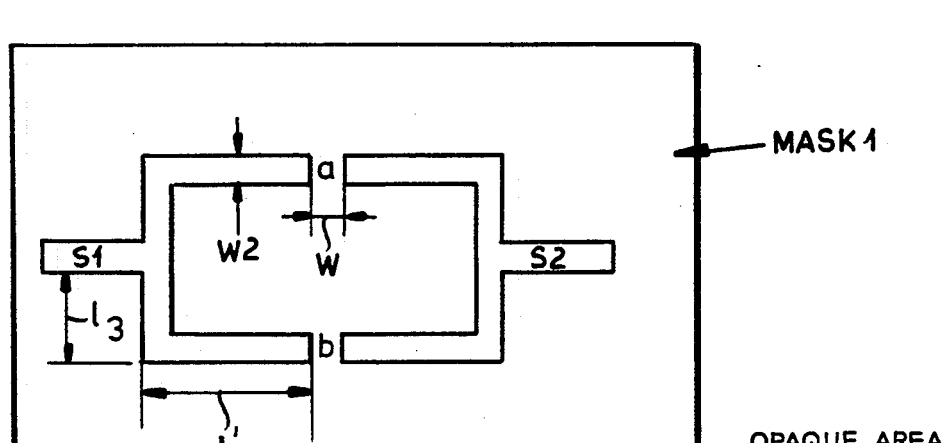
FIG. 7 is a plan view which shows schematically the mask of a SQUID.

In the present method, voltage noise, caused by asymmetric fluctuations of critical currents and other junction parameters of high Tc superconducting interference devices such as resistance, is eliminated while voltage signals only due to any flux change are preserved. With reference to the experimental arrangement of FIG. 1A, the high-Tc superconductor quantum interference devices may be made in the form of rectangular microstrips (see FIG. 1A and also FIG. 7 or rings of high-Tc superconducting thin films and insulator junctions denoted by X. The plane of the ring is perpendicular to the axis of the cylindrical metal rod or cylinder whose flaws/defects or mechanical stresses are to be detected, i.e., the plane is also perpendicular to the axis of the exciting coils. This arrangement ensures that the position of the said rod or cylinder is fixed rigidly with respect to that of the exciting coils. However the rod or cylinder can be moved through the coils if necessary. The primary fluxes are produced by fixed high frequency current (I) through oppositely wound coils c1 & c2 fed by a frequency $f_o$. This current is B amplitude modulated by fm frequency from the oscillator. This current is written as:

$$I = I_0[1 + 1\sin(2\pi f_1 t + \phi_1)]\sin(2\pi f_o t + \phi_o)$$

$$f_1 << f_o; 0 < 1 < 1$$

$\phi_1$ & $\phi_o$ are the corresponding phases.

For detection of flaws on the surface $f_o$ is generally high. Because of the modulation and opposite winding, the secondary fluxes consists of mainly low frequency $f_1$.

This primary flux will generate voltage in the superconductor quantum interference device. Because of the particular arrangement, the primary fluxes are of low frequency, $f_1$. This method has a high sensitivity of detection of the output signals due to the primary fluxes which are of high frequency, $f_o$. This method has a high sensitivity of detecting flaws and defects specially at the surface of the specimen. Alternately a single uniform exciting coil fed by an unmodulated low frequency excitation current can also be used. This latter procedure, though less sensitive can detect flaws and defects in depth of the specimen. The fluxes would have generated SQUID output voltages. Now an dc flux of $\phi_m = \phi_o/4$ for modulation at a frequency of $f_m$ is applied at the SQUIDs through the modulation coils M1, M2, M3 and M4 as shown in FIG. 1C & FIG. 2. This results in the modulated voltage of the SQUIDs. The $f_m$ component of the modulated voltage is denoted by $V_m(\phi)$ where $\phi$ is the flux to be detected and ultimately linked to defects and flaws in the specimen. As mentioned before, $V_m(\phi) = V(\phi + \phi_o/4) - V(\phi - \phi_o/4)$. When the bias current to the SQUID (see FIGS. 2 & 1c is alternated at frequency $f_b = f_m/8$ then one gets $V-_m(\phi)$ and $V+_m(\phi)$ at the output of the SQUID (not the output signal shown in FIG. 2). Both the modulation currents and the bias currents are derived from the same oscillator with the help of frequency dividers.

At the demodulator (FIG. 2) subtraction of $V+_m(\phi) - V-_m(\phi)$ is carried out and then integrated and a flux proportional to the said difference is fed back to the modulation coils when the feed back loop is closed. Thus a technique "flux-lock-loop-modulation with alternating bias currents" is achieved. The said subtraction is carried out at the demodulator using a reference signal with a reverse phase during the period of the negative bias current. This is achieved by using appropriate delay and dividers in FIG. 2. This method eliminates completely any noise that may result out of fluctuation of critical junction current and other parameters of SQUID which may be symmetric or asymmetric. The latter type of SQUID has two different values of critical currents for the two junctions.

For clarity it should be noted that a magnetic flux $\phi$ through a coil in general is the integration of the induced voltages $e = -d\phi/dt$ or $\phi = -\int edt$. The point G in FIG. 2 is where the modulation coils are connected. The other ends of the coils are ground.

Figure 4:
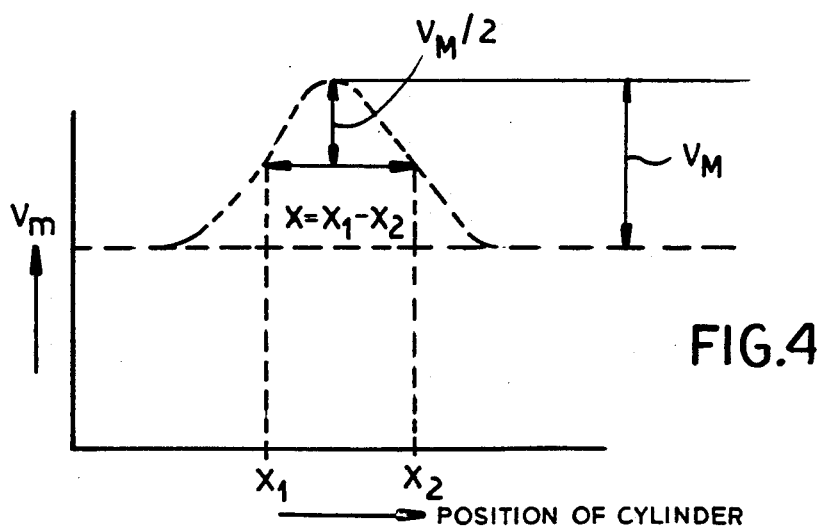
FIG. 4, is a graph which shows the general variation of the modulated voltage $V_m$ vs distance X of the metal cylinder within the exciting coil with reference to a fixed point.

Before inserting the test specimen, the voltage due to the primary coil flux can be nullified or zeroed by suitable adjusting certain circuit parameters such as the variable resistor or tank circuit in FIG. 2. This means that the superconductor quantum interference devices output voltage (see FIG. 2), due to the primary excitation flux, is made to be zero by adjustment in the absence of the test specimen. The test specimen, which in FIG. 2 is shown in the form of a cylinder, is inserted into the exciting coils c1 and c2, depicted in FIG. 1. The exciting currents now produce secondary magnetic field fluxes whose nature and distribution across the specimen depend on the characteristics of the defects and flaw present. Voltage readings of $V_m(\phi)$ or the output across the resistor (FIG. 2) are obtained which are indicators of the presence of said secondary fluxes. If the specimen is uniform and without any defect throughout, this voltage $V_m(\phi)$ is constant $(V_o)$ as the specimen is moved by sliding it in and out of the exciting coils c1 and c2. This state is shown by the straight dashed line in FIG. 3. If a flaw is present, the value of $V_m(\phi)$. or the output across the resistor (FIG. 2) at the flaw location deviates from the constant value, $V_o$. The shape of the $V_m(\phi)$ (shown by dotted lines) versus the position of rod, X, depends on the number of flaws present and their characteristics. A typical flaw curve is shown in FIG. 3 where, at the flaw location, the $V_m(\phi)$ curve deviates from the $V_o$ and one is able to measure the extent (the length) of the flaw by obtaining an average which is the distance between the half points X1 and X2. These points are located where the $V_m(\phi)$ would be half the maximum value, VM, as measured from the base line value Vo. The value of VM indicates the depth and nature of the flaw as well. FIG. 4 shows a typical $V_m(\phi)$, vs $\phi$ curve for positive and negative bias currents in asymmetrical SQUID.

It should be noted that this sensitive method does not necessarily require the high-$T_c$ SQUIDs to be placed in the vicinity of the specimen. The SQUIDs can be placed at any suitable location with the help of circuit of FIG. 1D. Where the pickup coil P is placed close to the specimen and the secondary coil with the help of a flux transformer T is placed close to the high-$T_c$ SQUIDs. The modulation coils M1, M2 etc. should, of course, be placed close to the SQUIDs.

In the case of ferromagnetic materials, mechanical stresses induced by thermal treatments affect their magnetic properties, especially the Barkhausen magnetic noise. This noise is due to the discontinuous change of magnetic induction as a function of magnetic field strength. I have determined that by periodically sweeping a given ferromagnetic sample with magnetic fields from superconductor excitation coils, which are fed by low frequency current (from a fraction of Hz to 50 Hz), Barkhausen noise can be produced and can be picked up at much higher frequencies, ranging from several KHz to 100 KHz. The shielding affect of the associated eddy currents limits Barkhausen noise to detection from a surface layer of limited thickness of the specimen (e.g., 50 microns). By measuring the magnetic characteristics, I have determined that evaluation of the mechanical stresses contained in the ferromagnetic material is possible. This is accomplished by using the high-$T_c$ superconductor quantum interference devices as magnetometers. Non SQUID or conventional SQUID magnetometers are known in the prior art to be useful for studying magnetic characteristics and stresses and defects in ferromagnetic materials.

I have determined also that the same experimental arrangement as shown in FIGS. 1A, 1B & 1C and FIG. 2 also can evaluate flaws and defects in ferromagnetic samples. However, one must include a dc bias magnetic field $H_{DC}$ as shown in FIG. 1B along the axis of the cylindrical sample. One can accomplish the dc bias magnetic field in a persistent mode through the use of flexible high-$T_c$ superconducting wires or tubes (see Ser. No. 08/300,287 filed 19 Jan. 1989). This means that the solenoid in FIG. 1B should then be made of the high-$T_c$ superconducting wires or tubes. In such case a high-$T_c$ superconducting switch as shown in FIG. 1F is needed. The coil P in that switch is the same as that wound around the solenoid in FIG. 1B. In FIG. 1F, the high-$T_c$ superconducting switch is a combination of a small size-high-$T_c$ superconducting coil 'S' and a resistor heater. 'S' is connected parallel to the coil P which is the same as the main field coil 13 of FIG. 1B. These are connected to the main power supply and immersed only in liquid nitrogen. To establish currents in P, the resistor heater is turned on until S becomes normal with resistance of several ohms; Voltage then develops across S and establishes current and hence magnetic field in P. The desired magnetic field is reached, the resistor is turned off and electrical current then circulates through P and S in a persistent mode.

The same electric circuit as shown in FIG. 2 for the use of high-$T_c$ SQUID can be used for the detection of the magnetic fluxes associated with the Barkhausen noises in the Ferromagnetic material. The magnetic field would be in a persistent mode. The direction of the field determines the directions along which flaws can be determined, i.e.—should coincide with the direction of movement of the rod within the excitation coils. Furthermore, instead of high frequency excitation currents, I have determined that I need excitation currents of low frequency. By periodically sweeping the fields generated by these low frequency excitation currents I can generate Barkhausen noise of high frequency, as stipulated earlier.

In yet another aspect of my invention, referred to as the second technique, high-$T_c$ SQUIDs, are used to measure the change in impedances of the exciting coils surrounding the metal plates that contain the flaws and defects in the plates. The latter affect the impedances of the coils.

FIG. 5a shows a frame F into which a metal plate M is introduced at a given speed. Frame F is made of non-conducting non-ferromagnetic material and is in the form of a rectangular hollow box. The box is wrapped with a primary excitation coil denoted by E. This coil is made of several turns of moderately thick copper wire. Reference character C denotes cables connected to BNC or other connectors. This frame is also wrapped (see FIG. 5) with a secondary coil or pick-up coil as denoted by P, with a large number of turns of fine wire. The metal plate to be tested for flaws is slowly inserted into the frame at a fixed speed. In the case of detecting defects in metal bodies of cars and airplanes, where the body to be analyzed is large, the E & P combinations are made deliberately small in a rectangular or circular form, connected to flexible cables. This structure is then moved at a constant speed across the surface of the said body to be analyzed.

Figure 6:
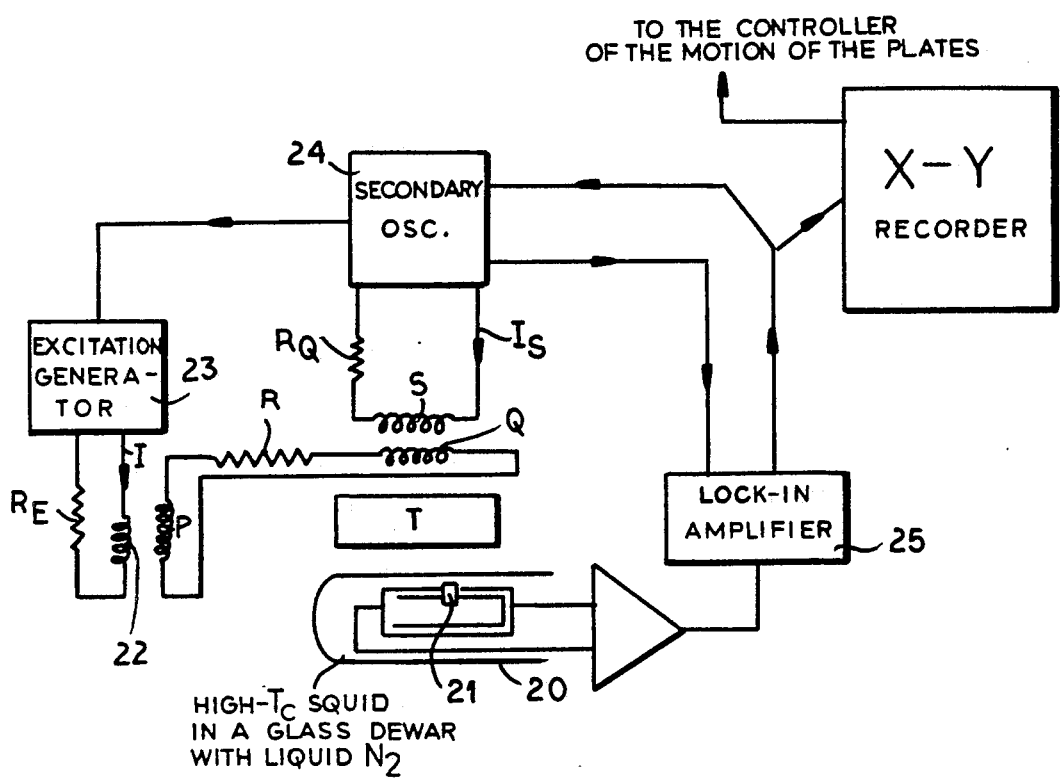
FIG. 6 is a circuit diagram which shows schematically the electronic circuits to measure the change of impedance of the coils E & P due to defects and flaws within the metals.

FIG. 6 illustrates operation of the electronic circuits employing high-$T_c$ SQUID, to measure the change in mutual inductance of the between the primary and the secondary coils. This can then related to the defects and flaws in the metal plate. The electronic circuit to measure the change in mutual inductance between coils is similar to that published by S. Barbanera, M. G. Castellano and V. Foglietti in Rev. Sci. Instrument 59, 1031 (1988).) Only one superconducting quantum interference device is shown but there may be several connected in series to the amplifier. This enhances the sensitivity of the overall measurement. The superconducting quantum interference devices are made of high-Tc superconducting materials. The plane of the said devices in FIG. 6 is arranged so as to obtain maximum flux from coils S & Q . T is a matching transformer of nominal ratio of 10:1. Because the superconducting quantum interference devices 21 are made of high-Tc superconductors (Tc= ~ 100 K.), they need to be placed in liquid $N_2$ or liquid oxygen. Their small size allows them to be inserted in glass tubes 20 as shown in FIG. 6 which are cooled by liquid $N_2$. If room temperature superconductors are used, such cooling is not necessary.

The great advantage of this technique is that the SQUIDs need not be placed in the vicinity of the specimen to be evaluated. In this mode, the superconducting quantum interference devices operate by means of amplitude modulated feed-back-loop null detection. In this method, the apparatus, as depicted in FIG. 6, becomes sensitive to an inbalance of the two magnetic fluxes due to changes in mutual inductance only. This design has proven to be totally insensitive to resistance variations of the input circuits caused by temperature changes. Defects in metals can be measured by changes in the mutual inductance of these coils, as well as their impedance. Both the primary coil E and the pickup coil P, are affected by a net change of magnetic fluxes when a defect is present in the metal. However, I have found that the magnetic fluxes due to the primary excitation coil and the eddy current generated by it in the metal plate do not directly affect the voltage or the current of the high-Tc superconducting quantum interference device. The latter is made to be affected only when defects and flaws are present in the metal.

With reference to FIG. 6, a current, I, is supplied to the exciting coil 22, through a resistance $R_E$ of about 100–1000 ohm, in series with the coil 22. A Hewlett-Packard model 3325A synthesizer 23 may be used for this purpose. The current is adjusted so that a peak field of ~1G is produced within frame F (FIG. 5a). The frequency of excitation current is dependent on the nature of defects and flaws and also types of metal to be investigated. This has been mentioned earlier. Similarly, a secondary generator supplies currents, $I_s$, to coil, S, which couples another coil, Q, by mutual inductance, $M_{sq}$. When the mutual inductance of E and P is $M_{ep}$, the coils are designed so that Msq and Mep are almost equal. Though it is not a necessary condition, this mode simplifies the operation of the device for the non-destructive evaluation of metals:

$$I = I_0 \sin(2\pi f_0 t + \phi_0)$$

Excitation current, I, results in a magnetic flux, $\phi_m$, which is proportional to the mutual inductance Mep between coils, E and P. A magnetic flux, $\phi_q$, alternating at the same frequency, $f_o$, is also coupled to the circuit by means of mutual inductance, $M_{qs}$, between coils Q and S. This flux is fed by a secondary generator through resistance, $R_Q$. The amplitude and phase of this generator is controlled by the feedback loop to ensure the nulling of the two fluxes at the SQUID, and the two generators are phase locked to each other. T is a matching transformer with nominal ratio of 10:1. This will enhance the coupling of fluxes to the SQUID. For maximum sensitivity, the plane of the thin film high-$T_c$ SQUID should be normal to the magnetic fluxes. One initially works with the first generator, setting its amplitude to a suitable constant value by noting the superconducting quantum interference device output voltage. Then with the first generator switched off and the second oscillator switched on, the amplitude is again set to achieve an output voltage equal to that of the previous step.

With the two generators now turned on simultaneously, the relative phase between them can now be carefully adjusted in order to null the emf generated due to the two resulting fluxes $\phi_m$ and $\phi_q$ in the superconducting quantum interference device. The feed back loop is then closed and the superconducting quantum interference device output is passed through a lock-in amplifier 25 referenced at the working frequency. The lock-in output is connected to the amplitude modulation input of the secondary oscillator (see FIG. 4). As $\phi_m$ and $\phi_q$ are balanced, first the lock-in output and then the feed back signal are zero. This is the null condition.

The metal plate to be tested for flaws is then inserted in frame F of FIG. 5A (Note that the same coils E and P are in FIG. 6) The resulting change in the mutual inductance Mep offsets the previously obtained null condition and even a small offset in flux is greatly magnified by the transformer, T, and a signal due to which is detected by the lock-in amplifier. This signal is then used to adjust the amplitude of the second oscillator to a new equilibrium value. (The signal from the first generator is fixed after the first null condition is obtained). The output signal of the lock-in amplifier is also the output of the entire feedback system. The transfer function of the system in closed-loop configuration is determined by the reverse transfer function due to the high value of the open-loop gain:

$$V_{out}/DM_{ep} = RF_{im}/aM_{sq}$$

where $V_{out}$ is the lock-in amplifier output; $DM_{ep}$ is the change of the mutual inductance due to the defects in the metal plate; and a is the amplitude modulation coefficient of the second oscillator. The value of $M_{sq}$ can be determined, for example, at the open loop by turning off the second generator and measuring the amplitude of the first oscillator and the output of the superconducting quantum interference device. The detection of $DM_{ep}$ is due to the defects and flaws, present in the metal.

To obtain precise information about the defects, their nature must first be understood: their size, shape and depth beneath the surface of the metal, and the changes of mutual inductance DMep of the coils of given configuration such as those in FIG. 6. To accomplish this, an identical but defect free metal plate M is slowly inserted at a fixed speed in frame F (FIGS. 5a and 6). The previously obtained null condition then changes and the X-Y recorder records signal ($S_p$) due to the faultless metal plate. After this plate is removed, the same null condition is ensured to exist in the output of the high-Tc superconducting quantum interference devices. The metal plate with faults is then inserted into the frame at the same speed. The exact location of where faults lie is indicated in the signal recorded in the X-Y recorder by marked changes in the signal output ($S_f$). Since the speed of insertion of the plate is known, the X-axis of the X-Y recorder indicates the X position of the metal plate relative to the frame. Thus the positions of the defects in the plate are detected by comparing the two signals $S_p$ and $S_f$. If the defect sizes are large or very close to the surface, changes in signals $S_f - S_p$ will be stronger at that point. The profile of the $S_f - S_p$ signals indicate the X-profile of the faults in the metal plate. Similary, the Y-profile can also be obtained by rotating the plate through 90° and following above procedures. To detect defects and flaws which are buried deep beneath the surface, the frequency of excitations (generators 23 and 24 in (FIG. 6) is reduced and the amplitude of oscillations is increased. High frequency limits the penetration of the primary excitation to the skin depth of the metal. Reducing the frequency allows defects at greater depths to be measured. To measure defects in a ferromagnetic material a dc magnetic field bias should be provided. This can be done as discussed before with flexible high-$T^c$ superconducting coils or tubes in a persistent mode.

The SQUID circuit can be fabricated in a simple way. This schematically shown in FIG. 7. The mask for the SQUID of proper design is prepared (See FIG. 8. In this mask the high-$T_c$ superconducting lines are shown as transparent to the incident light (UV) and the insulating junctions are opaque. The mask is kept as shown in FIG. 8 and exposed to ArF excimer laser light from a laser source 32. The laser light passes through the transparent portion of the mask 32 and enters the chamber 31. In the chamber 31 the substrate 33 on which high-$T_c$ SQUID is placed on the substrate stage 34 as shown. This substrate is coated with insulating materials like MgO, $SiO_2$, $SrTiO_3$ about 1-3 micron thick. The substrates can be chosen as mentioned earlier. It is heated to 200° C. The substrate stage is grounded as shown in FIG. 8. A ring electrode 35 creates oxygen plasma when connected to about 1000 V in a glow discharge. Oxygen gas from the cylinder 36 passes through the mixture containing stoichiometric ratio of TMC, TMY and TMBa. TMC stands for trimethyl copper; TMY stands for trimethyl yttrium and TMBa stands for trimethyl barium. These are liquids at room temperature but vaporizes easily when a gas passes through the liquid. The mixture is such that it contains the ratio of the metals say Y, Ba and Cu in the same ratio as they appear in a high-$T_c$ superconductor ceramic composition.

The pressure of the vapor mixtures in the chamber is controlled by regulating the oxygen flow as shown. The ArF excimer laser pulse should be around 8-12; the repetition rate should be around 100-120 pps. Laser light then reacts photochemically with the vapors and deposits metals from the vapor on to the substrate. It may also deposit same on the entrance window. Therefore oxygen is led to flow over the window in order to prevent blocking of the window by the deposited metals and vapors. If the oxygen pressure is around 50-100 m torr then diffusion of the deposited metals outside the projections corresponding to the transparent lines can be minimized. This will led to writing of fine metals lines which is the uniform and stoichiometric mixture of three metals say Y, Ba and Copper. After depositing the metal film of appropriate thickness which depends on vapor pressure, laser light intensity, pulse width, pulse rate and substrate temperature, the flow of TMC, TMY and TMBa vapors are discontinued. The oxygen flow is still maintained and oxygen plasma between the ring electrode and the substrate stage is created by applying dc potential of the order of 300–1000 volts depending on oxygen pressure. A typical oxygen pressure could be around 1 m torr. The substrate temperature may be raised to about 400° C. The annealing of the said deposited metal films would make the films high-$T_c$ superconducting in about 30–60 minutes. This process can be improved by those skilled in the art to suppress completely any probable diffusion of the photolytic metallic fragments on to the neighboring microstrip lines. Such process then will become very efficient By this technique of direct laser writing of microstrip superconducting lines SQUIDs can be prepared without going through details of photolithographic processes and thus will save considerable time and labor.

EXAMPLES

1. The apparatus of FIG. 1C is used. Before inserting the metal test specimen, the primary coil flux signal is nulled by adjusting the output voltages of the superconductor quantum interference devices, as described above. The test specimen is next inserted within the test coils at a controlled speed. If the specimen is uniform and without defects, a continuous voltage line will result. Any defects present will cause a deviation from the said line. The point of deviation can be correlated to the specific point within the specimen where the enclosed defect lies. In most cases, there will be a number of defects present and a "flaw curve" will result. The extent and length of any sizable flaw can be directly measured by using an average deviation from the base line.

2. In the case of ferro-magnetic materials, the apparatus of FIG. 1C can also be employed. I can use a uniform dc magnetic field (FIG. 1B) parallel to the axis of the cylindrical ferromagnetic material. The field is produced by a solenoid shaped coil that covers the entire length of the cylinder. In such cases all other coils like c1, c2, M1, M2 of FIG. 1A & FIG. 1B should be inside the solenoid coils. For persistent mode of operation this dc field could be generated by a high-$T_c$ superconducting flexible coil as mentioned before. The electrical supplies for the superconductor excitation coils are fed a low frequency current ranging from a few Hz to about 50 Hz. This induces a Barkhausen effect in the specimen which is shielded by the associated eddy currents. The output of the superconductor excitation coils is connected to a magnetometer. The low frequency current is swept through the said coils in a cyclic manner while the specimen is being moved through the magnetic fields produced by the superconductor excitation coils. A correlation of the magnetometer signal with position of the specimen within the said coils allows the detection of flaws within the ferro-magnetic specimen being tested.

3. It should be noted that this sensitivity does not necessarily require the high-$T_c$ SQUIDs to be placed in the vicinity of the specimen as is shown in FIG. 1C. The SQUIDs can be placed at any suitable location with the help of circuit of FIG. 10. Where the pickup coil P is placed close to the specimen and the secondary coil with the help of a flux transformer T is placed close to the high-$T_c$ lfcSy SQUIDs. The modulation coils M1, M2 etc. should of course be placed close to the SQUIDs. This arrangement can increase the maneuverability of the apparatus.

4. With reference to FIGS. 5a, 5b and 6, a current, I, is supplied to the exciting coil, E, through a resistance of about 100–1000 ohm. A Hewlett-Packard model 3325A synthesizer may be used for this purpose. The current I is adjusted so that a peak field of $\sim$1G is produced within frame F (FIG. 5a). Similarly, a secondary generator supplies currents, Is, to coil, S, which couples another coil, Q, by mutual inductance, $M_{sq}$. When the mutual inductance of E and P is Mep (see FIGS. 5a, 5b and 6), the coils are designed so that $M_{sq}$ and $M_{ep}$ are almost equal. This mode simplifies the operation of the device for the non-destructive evaluation of metals. The metal plate to be tested for flaws is then inserted in frame F of FIG. 5a. (Note that the same coils E and P are shown in FIG. 6). The resulting change in the mutual inductance $M_{ep}$ offsets the previously obtained null condition and a signal is detected by the lock-in amplifier. This signal is then used to adjust the amplitude of the second oscillator to a new equilibrium value. (the signal from the first generator is fixed after the first null condition is obtained). The output signal of the lock-in amplifier is also the output of the entire feedback system. The transfer function of the system in closed-loop configuration s determined by the reverse transfer function due to the high value of the open-loop gain.

The sensitivity of the detection will increase significantly if the coils E & P are made of flexible high-$T_c$ superconducting wires.

I claim:

1. A method of nondestructive evaluation of locations of flaws in a metal body, comprising the steps of:
    (a) positioning a high-critical-temperature superconductive quantum interference device having a pair of insulated junctions in a superconductor loop in a flux-sensing relationship to a location adjoining said body;
    (b) relatively displacing said body and said location;
    (c) while said body and said location are relatively displaced, exciting said body with a modulated alternating current and detecting with said device flux irregularities representing flaws in said body;
    (d) establishing locations of said flaws by the relative positions of said location and said body upon the detection of said flux irregularities, a plurality of said devices being connected in series are juxtaposed with said body;
    (e) demodulating a signal generated by the series-connected devices to form an output; and
    (f) connecting respective modulating coils inductively coupled to the respective high-critical-temperature superconductive quantum interference devices and connected to said output in a feedback path to form a flux-locked loop with said high-critical-temperature superconductive quantum interference devices.

2. The method defined in claim 1 wherein said body is excited in step (c) by passing an alternating current through two series-connected coil wound in opposite senses around said body, said alternating current having a frequency between substantially 1 kHz and 1 MHz and being modulated with a modulating frequency which is a fraction thereof.

3. The method defined in claim 2, further comprising the step of energizing said modulation coils with a square-wave signal of a frequency of 10 kHz to 500 kHz modulated with a frequency of ½ to 1/20 of the frequency of the square-wave signal.

4. The method defined in claim 3 wherein said square-wave signal is modulated with a frequency which is ½ of the frequency of the square-wave signal.

5. The method defined in claim 2 wherein said body is composed of a ferromagnetic material, further comprising the step of applying a constant unidirectional magnetic field to said body as a bias magnetic field during nondestructive evaluation of the body.

6. The method defined in claim 2 wherein four of said high-critical-temperature superconductive quantum interference devices are juxtaposed with said body and constitute two parallel-connected pairs of series-connected high-critical-temperature superconductive quantum interference devices.

7. A method of nondestructive evaluation of locations of flaws in a metal body, comprising the steps of:
 (a) positioning a high-critical-temperature superconductive quantum interference device having a pair of insulated junctions in a superconductor loop in a flux-sensing relationship to a location adjoining said body;
 (b) relatively displacing said body and said location;
 (c) while said body and said location are relatively displaced, exciting said body with a modulated alternating current and detecting with said device flux irregularities representing flaws in said body; and
 (d) establishing locations of said flaws by the relative positions of said location and said body upon the detection of said flux irregularities, said location being defined by a coil juxtaposed with said body and connected in series with a coil located remote from said body, said high-critical-temperature superconductive quantum interference device being juxtaposed with said coil located remote from said body.

8. A method of nondestructive evaluation of locations of flaws in a metal body, comprising the steps of:
 (a) positioning a high-critical-temperature superconductive quantum interference device having a pair of insulated junctions in a superconductor loop in a flux-sensing relationship to a location adjoining said body;
 (b) relatively displacing said body and said location;
 (c) while said body and said location are relatively displaced, exciting said body with a modulated alternating current and detecting with said device flux irregularities representing flaws in said body;
 (d) establishing locations of said flaws by the relative positions of said location and said body upon the detection of said flux irregularities, said location being defined by a coil juxtaposed with said body and connected in series with a coil located remote from said body; and
 (e) inductively coupling said coil located remote from said body with said high-critical-temperature superconductive quantum interference device.

9. An apparatus for nondestructive location of flaws in a metal body, comprising:
 a high-critical-temperature superconductive quantum interference device having a pair of insulated junctions in a superconductor loop disposed in flux-sensing relationship to a location adjoining said body;
 means for relatively displacing said body and said location;
 means for exciting said body with a modulated alternating current while said body and said location are relatively displaced, whereby said device detects flux irregularities representing flaws in said body;
 means for establishing locations of said flaws by the relative positions of said location and said body upon the detection of said flux irregularities, a plurality of said devices connected in series being juxtaposed with said body,
 means for demodulating a signal generated by the series-connected devices to form an output; and
 respective modulating coils inductively coupled to the respective high-critical-temperature superconductive quantum interference devices and connected to said output in a feedback path to form a flux-locked loop with said high-critical-temperature superconductive quantum interference devices.

10. The apparatus defined in claim 9 wherein said body is excited in step (c) by passing an alternating current through two series-connected coils wound in opposite senses around said body, said alternating current having a frequency between substantially 1 kHz and 1 MHz and being modulated with a modulating frequency which is a fraction thereof.

11. The apparatus defined in claim 10, further comprising means for energizing said modulation coils with a square-wave signal of a frequency of 10 kHz to 500 kHz modulated with a frequency of ½ to 1/20 of the frequency of the square-wave signal.

12. The apparatus defined in claim 9 wherein said body is composed of a ferromagnetic material, further comprising means for applying a constant unidirectional magnetic field to said body as a bias magnetic field during nondestructive evaluation of the body.

13. The apparatus defined in claim 9 wherein four of said high-critical-temperature superconductive quantum interference devices are juxtaposed with said body and constitute two parallel-connected pairs of series-connected high-critical-temperature superconductive quantum interference devices.

14. An apparatus for nondestructive location of flaws in a metal body, comprising:
 a high-critical-temperature superconductive quantum interference device having a pair of insulated junctions in a superconductor loop disposed in flux-sensing relationship to a location adjoining said body;
 means for relatively displacing said body and said location;
 means for exciting said body with a modulated alternating current while said body and said location are relatively displaced, whereby said device detects flux irregularities representing flaws in said body; and
 means for establishing locations of said flaws by the relative positions of said location and said body upon the detection of said flux irregularities, said location being defined by a coil juxtaposed with said body and connected in series with a coil located remote from said body, said high-critical-temperature superconductive quantum interference device being juxtaposed with said coil located remote from said body.

15. An apparatus for nondestructive location of flaws in a metal body, comprising:
- a high-critical-temperature superconductive quantum interference device having a pair of insulated junctions in a superconductor loop disposed in flux-sensing relationship to a location adjoining said body;
- means for relatively displacing said body and said location;
- means for exciting said body with a modulated alternating current while said body and said location are relatively displaced, whereby said device detects flux irregularities representing flaws in said body;
- means for establishing locations of said flaws by the relative positions of said location and said body upon the detection of said flux irregularities, said location being defined by a coil juxtaposed with said body and connected in series with a coil located remote from said body; and
- means for inductively coupling said coil located remote from said body with said high-critical-temperature superconductive quantum interference device.

* * * * *